United States Patent [19]

St. Pierre et al.

[11] Patent Number: 5,236,701
[45] Date of Patent: Aug. 17, 1993

[54] INGESTIBLE HYDROPHILIC POLYMERIC AMINES USEFUL FOR LOWERING BLOOD CHOLESTEROL

[75] Inventors: Leon E. St. Pierre, Frelighsburg; George R. Brown, Dollard-des-Ormeaux; Gaoming Wu, Montreal, all of Canada

[73] Assignee: Lowchol Scientific Inc., Frelighsburg, Canada

[21] Appl. No.: 381,988

[22] Filed: Jul. 19, 1989

[51] Int. Cl.$^5$ .............................................. A61K 31/74
[52] U.S. Cl. ............................... 424/78.12; 424/78.1; 424/78.11; 525/329.4
[58] Field of Search ............. 525/329.4; 424/78, 78.1, 424/78.21, 78.11, 78.12, 78.13, 78.14

[56] References Cited

U.S. PATENT DOCUMENTS

| | | | |
|---|---|---|---|
| 3,308,020 | 3/1967 | Wolfe et al. | 167/65 |
| 3,733,400 | 5/1973 | Queuille et al. | 424/81 |
| 3,787,474 | 1/1974 | Daniels et al. | 424/78.1 |
| 4,082,701 | 4/1978 | Fries et al. | 260/2.1 E |
| 4,115,550 | 9/1978 | Fields et al. | 424/78.21 |
| 4,211,765 | 7/1980 | Johnson et al. | 424/78 |
| 5,114,709 | 5/1992 | Pierre et al. | 424/78.12 |

FOREIGN PATENT DOCUMENTS 3001856 7/1981 Fed. Rep. of Germany .

OTHER PUBLICATIONS

"Concise Encyclopedia of Polymer Science & Engineering", Ed., Kroschwitz, J. I., J. Wiley & Sons, Publisher, N.Y., pp. 213-217.
Wallace, J. S., & Morrow, C. J., "Biocatalytic Synthesis of Polymers.II—Preparation of [AA-BB]$_x$ Polyesters by Porcine Pancreatic Lipase Catalized Transesterification in Anhydrous, Low Polarity Organic Solvents", J.Polymer.Sci: Part A:Polymer.Chem.27:32-71-3284(1989).
"The Merck Index", Ed., Windholz, M., Merck & Co., Inc. Publisher, Rathway, N.J.,(1983),p. 410.
Winne, D., & Gorig, H., "Appearance of $^{14}$C-Polyethylene Glycol 4000 in Intestinal Venous Blood:Influence of Osmolarity and Laxatives, Effect on Net Water Flux Determination", Archives of Pharmacology. 321:149-156(1982).

*Primary Examiner*—Paul R. Michl
*Assistant Examiner*—Tae H. Yoon
*Attorney, Agent, or Firm*—Viviana Amzel

[57] ABSTRACT

The invention is concerned with novel ingestible cross-linked homopolymers having functional groups consisting of linear or branched amines, of the formula:

$$P-[(CH_2)_nNR]_mR \quad \text{(Ia)}$$

or

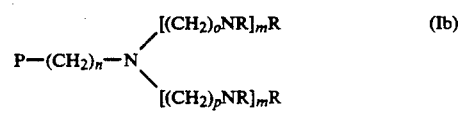
(Ib)

and their pharmaceutically acceptable salts of the formulae:

$$P-[(CH_2)_nN^+(R)_2]_mR.mX^- \quad \text{(Ic)}$$

and

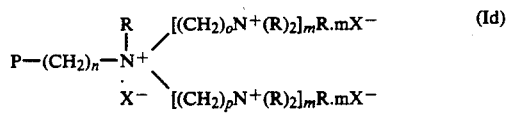
(Id)

wherein P represents a hydrophilic, cross-linked and non-digestible homopolymer backbone; R is a hydrogen atom or a lower alkyl radical; X$^-$ is a pharmaceutically acceptable anion; m is an integer varying from 1 to 10 inclusive; and n, o and p are, independently, integers varying from 2 to 12 inclusive. The amine functionalized and cross-linked homopolymers of the invention are highly efficient adsorbents for bile acids and salts and can thus be used for reducing hypercholesterolemia in affected humans.

13 Claims, 4 Drawing Sheets

INGESTIBLE HYDROPHILIC POLYMERIC AMINES USEFUL FOR LOWERING BLOOD CHOLESTEROL

The present invention relates to novel ingestible amine functionalized and cross-linked homopolymers which are useful as adsorbents for salts. More particularly, the invention is directed toward the treatment of hypercholesterolemia by removing through adsorption the bile acids and salts from the small intestine, thereby increasing the catabolism of cholesterol in the liver with a concomitant decrease in the blood cholesterol level.

Elevation of the blood cholesterol, hypercholesterolemia, is widely considered as a major risk factor for the development of atherosclerosis and cardiovascular diseases. It is presently the leading cause of death of adults in most of the developed countries. Over the last few decades, researchers have focussed their attention on lowering the cholesterol level in the blood to reduce the risk of cardiovascular diseases. This can be achieved with limited success by reducing in the cholesterol intake from food sources and accelerating the elimination of cholesterol from the human body, although genetic factors can also be important. In severe cases, the disease can be treated clinically by oral drugs, surgery, hemoperfusion or a combination of these treatments.

Biologically, cholesterol is eliminated from the human body by conversion to bile acids and excretion as neutral steroids. Bile acids are synthesized daily from cholesterol in the liver and enter the bile as glycine and taurine conjugates. They are released in salt form with bile during digestion. Bile salts are mostly reabsorbed in the ileum with only about 1% loss per cycle, complexed with proteins and returned to the liver through hepatic portal veins. This small loss of bile salts represents a major route for the elimination of cholesterol from the body.

The available prescription drugs interrupt either the biosynthesis of cholesterol in the body or the enterohepatic circulation of bile salts. Some of the inhibitors for the biosynthesis of cholesterol, such as lovastatin (Mevinolin), are reported to be significantly effective. Their clinical usefulness is limited however, due to some of their untoward side effects. Medicines acting as adsorbents, such as cholestyramine and colestipol, bind bile salts in the small intestine, thus preventing the reabsorption of bile salts. The fecal excretion of bile salts is enhanced under the effect of cholestyramine and, therefore, the conversion of cholesterol to bile acids is accelerated to maintain the bile pool. However, both cholestyramine and colestipol have major side effects which include the bad taste and the dryness of cholestyramine, low adsorption capacity of colestipol, and their poor biological compatibilities.

Cholestyramine, the most widely used adsorbent for bile salts, is a copolymer of polystyrene and divinylbenzene with quaternary ammonium groups as functional groups. Being a typical strongly basic ion exchanger, its counterions of the quaternary ammonium, usually chloride ions, are exchanged with bile salt anions during the binding. The hydrophobic nature of the polymer backbone results in its poor biocompatibility. As a consequence, adverse side effects have been experienced by hypercholesterolemic patients. The drug has to be taken in large dosage and may cause stomach discomfort to patients.

It is therefore an object of the present invention to overcome the above drawbacks and to provide novel bile salt adsorbents with high adsorption capacity, good biocompatibility and improved taste.

In accordance with the invention, there is provided a novel cross-linked homopolymer having functional groups consisting of linear or branched amines of the formula:

  (Ia)

or

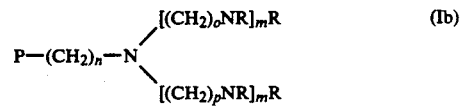  (Ib)

as well as the pharmaceutically acceptable salts thereof having the formulae:

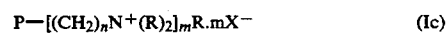  (Ic)

and

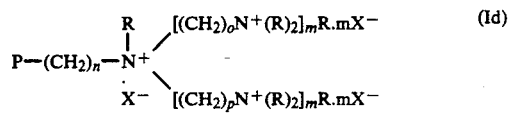  (Id)

wherein:

P represents a hydrophilic, cross-linked and non-digestible homopolymer backbone;

R is a hydrogen atom or a lower alkyl radical;

$X^-$ is a pharmaceutically acceptable anion;

m is an integer varying from 1 to 10 inclusive; and n, o and p are, independently, integers varying from 2 to 12 inclusive.

It has been found quite unexpectedly that the above polymeric compounds exhibit increased hydrophilicity and are highly efficient adsorbents for cholic acid and glycocholic acid as well as other bile acids, such as chenodeoxycholic acid, lithocholic acid, deoxycholic acid and taurocholic acid. The significance of the bile acid adsorption is related to the lowering of serum cholesterol. As it is known, cholesterol is a major and probably the sole precursor of bile acids during normal digestion, bile acids are secreted via the bile from the liver and the gallbladder into the intestine. Bile acids emulsify the fat and lipid materials present in the foods, thus facilitating adsorption. A major portion of bile acids secreted is reabsorded from the intestines and returned via the portal circulation of the liver, thus completing the enterohepatic cycle. The binding of bile acids in the intestines onto an insoluble adsorbent that is excreted in the feces results in partial removal of bile acids from the enterohepatic circulation, preventing their readsorption. The increased fecal loss of bile acids leads to an increased oxidation of cholesterol to bile acids, a decrease in beta lipoprotein or low density lipoprotein serum levels, and a decrease in serum cholesterol level. Thus, the compounds of the invention can be used for reducing hypercholesterolemia in affected humans.

Accordingly, the present invention also provides, in a further aspect thereof, a method of treating hypercholesterolemia in an affected human, which comprises administering to the affected human an effective amount of a bile salt adsorbent consisting of an amine functionalized and cross-linked homopolymer as defined above.

According to yet another aspect of the invention, there is provided a pharmaceutical composition for the treatment of hypercholesterolemia, which comprises as active ingredient an amine functionalized and cross-linked homopolymer as defined above, together with a pharmaceutically acceptable carrier therefor.

The polymer backbone to which the amino groups are chemically bonded must be hydrophilic so as to swell in an aqueous medium. This ensures good contact with the medium and also opens the pores in the polymer so that there is good access to all of the functional groups. The polymer backbone must also be cross-linked to prevent the adsorbent from diffusing from the digestive tract, as well as non-digestable to prevent the adsorbent from being broken down and absorbed into the body. It is preferably porous to permit diffusion of the bile salts which are to be sequestered, thereby improving adsorption capacity.

A preferred polymer resin for use as backbone to which the amino groups can be attached is a porous, cross-linked polymethylacrylate resin. Such a resin is advantageously prepared by polymerizing methyl acrylate in the presence of two cross-linking agents used in a ratio of 1:1.

Particularly preferred amine-containing resins according to the invention are the homopolymers functionalized with linear amines of formula (Ia) and their protonated and quaternized derivatives of formula (Ic), in which R is a hydrogen atom or a methyl radical, m is 1, 2 or 3, n is 2 or 3, P represents a polyacrylamide resin and $X^-$ is a pharmaceutically acceptable anion such as $Cl^-$, $I^-$ or $OH^-$.

Amongst the homopolymers functionalized with branched amines of formula (Ib) and their protonated and quaternized derivatives of formula (Id), the preferred compounds are those in which R is a hydrogen atom or a methyl radical, m is 1, n, o and p are each 2, P represents a polyacrylamide resin and $X^-$ is a pharmaceutically acceptable anion.

The amine-containing resins according to the invention not only exhibit high adsorption capacity but also high water-swellability, which render them suitable for clinical application.

Further features and advantages of the invention will become more readily apparent from the following non-limiting examples and the accompanying drawings, in which:

1. PREPARATION OF POLYMER BACKBONE

Figure 1:
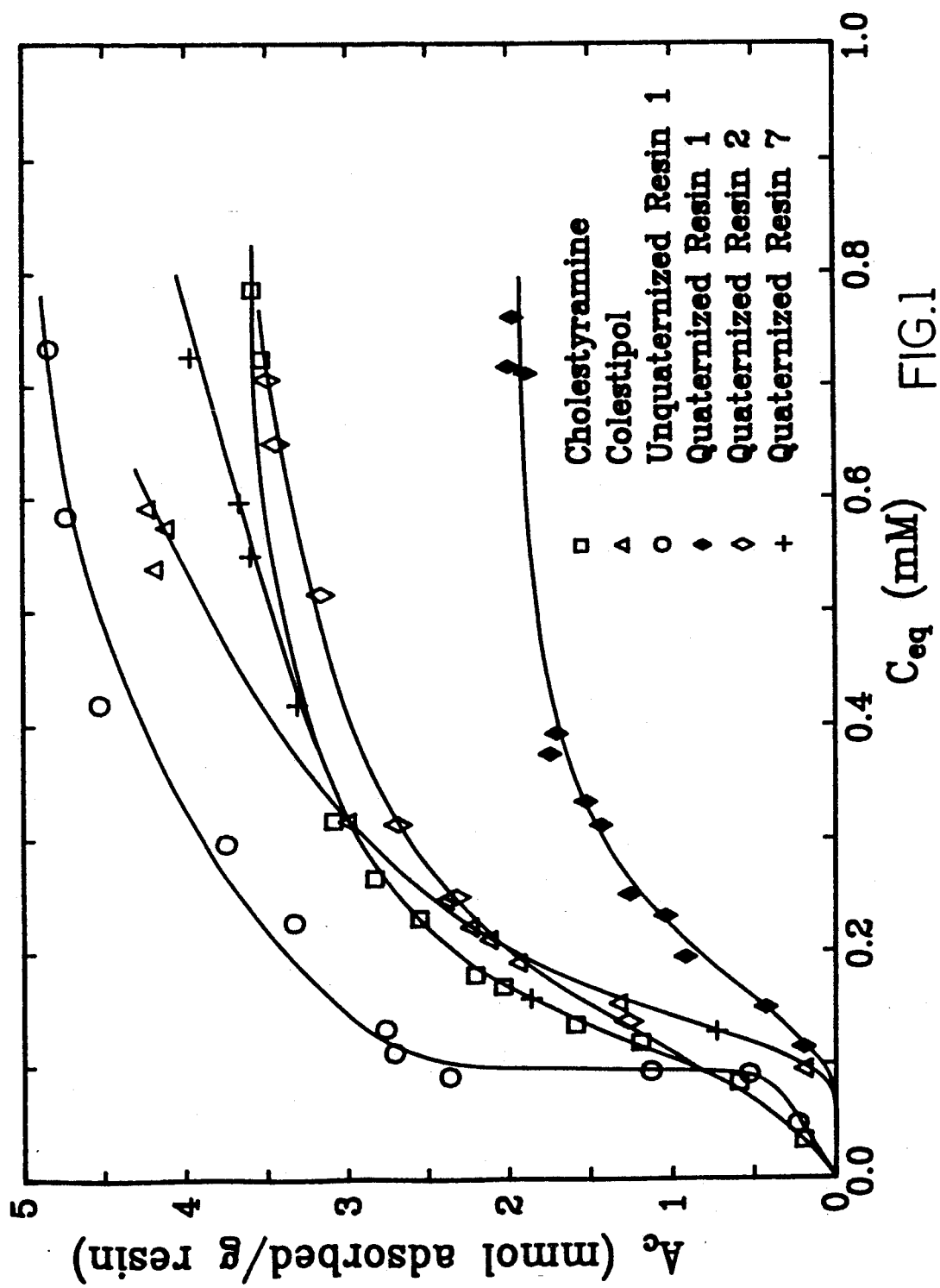
FIGS. 1 and 2 show the adsorption isotherms of compounds according to the invention for sodium glycocholate in 0.0025M, pH 7.1 Tris buffer, compared with the adsorption isotherms of cholestyramine and colestipol (used as reference adsorbents)

A suitable carrier resin was synthesized by polymerizing methyl acrylate in the presence of cross-linking agents to form a porous, cross-linked polymethylacrylate (PMA) resin.

The polymerization was carried out in a 1000 ml 3-necked flask equipped with a mechanical stirrer and a condenser. Into the flask, 25 grams of NaCl and 480 ml distilled water were added. The solution was stirred until all of the NaCl has been dissolved. The temperature of the water bath was set at 50° C. 120 ml of 2% polyvinyl alcohol (PVA) solution was added and the solution was mixed. The position of the stirring blade was adjusted so that the top of the blade was at the surface of the water phase.

In a separate beaker, 94 grams of methyl acrylate, 3.0 grams of each of the cross-linking agents, divinyl benzene and triallyl-1,3,5-triazine-2,4,6-(1H,3H,5H)-trione, and 1.4 grams of benzoyl peroxide were added. The benzoyl peroxide was allowed to dissolve completely Then 20-25 grams of butyl ether was added and the contents were well mixed.

This mixture was then added to the contents of the 1000 ml flask, and formed an oil phase. Stirring was then commenced with the speed being controlled so as to yield the appropriate bead size for the carrier resin.

The temperature of the water bath was then increased slowly (8° C./ hr) until it reached 60° C., and then increased more slowly (4° C./ hr) to 68° C. The system was maintained at this temperature for 24 hours, following which the polymerization was continued for 24 hours at 80° C. and another 24 hours at 95° C.

The product was cooled and washed repeatedly with warm water to remove the PVA. It was then washed by refluxing methanol for 24 hours to remove butyl ether and soluble polymer species. The carrier resin thus obtained was ready for functionalization.

2. FUNCTIONALIZATION OF POLYMER BACKBONE

A 200 ml 3-necked flask equipped with a mechanical stirrer, a condenser, a thermometer, $CaCO_3$ drying tube was immersed in an oil bath. 5 grams of PMA and 100 ml of an alkyldiamine were added into the flask and stirred for one hour at room temperature. The temperature was then increased to 50° C. and was maintained for 3 hours. Thereafter it was increased to 120° C., and maintained at this temperature for 4 days. The amine-containing resin thus obtained was repeatedly washed with methanol, and then with distilled water. It was finally dried under vacuum.

3. QUATERNIZATION OF THE AMINE-CONTAINING RESINS

A 500 ml 3-necked flask equipped with mechanical stirrer, a condenser to which a $CaCO_3$ drying tube was attached, a thermometer was immersed in an oil bath. 5 grams of amine-containing resin prepared above, 25 grams of $KHCO_3$ and 150 ml methanol were added into the flask. After 2 hours of stirring at 35° C., 80 ml of methyl iodide was added. The reaction was maintained for 4 days in the dark. The final product was repeatedly washed with methanol, with distilled water, with concentrated NaCl solution, and eventually with water.

4. PROTONATION OF THE AMINE-CONTAINING RESINS

The amine-containing resins were treated with dilute hydrochloric acid solution at room temperature to convert the free amine groups to positively charged organic ammonium groups. This can be done either in a column where dilute HCl passes through the column until the protonation is complete, or simply in a container where an excess amount of hydrochloric acid is in contact with the resin (standing or shaking). Then the excess hydrochloric acid was washed away with a large amount of distilled water until the resin is neutral.

5. CHARACTERIZATION OF THE ADSORBENTS

The products were characterized both qualitatively by infrared spectroscopy and quantitatively by acid-base back titration. IR results proved that the ester groups in the former PMA backbone had been converted to amide groups and the amine-containing small molecules have been chemically attached to the polymer backbone as expected. From acid-base back titration, it was found that all of the products were nitrogen rich materials and that they had subtitutions (free base or protonated or quaternized nitrogen) of about 2–8 mmol/g.

6. ADSORPTION STUDIES (a). Adsorption studies in Tris buffer

Tris(hydroxymethyl)-aminomethane (Aldrich) and 1.000N standard HCl solution were used to prepare a buffered solution with ionic strength 0.0025M and pH 7.1. With this buffer, bile salt solution with concentration about 50 mg/dl was prepared and was used directly. Into bottles of different sizes (2–100 ml), about 5–15 mg of the resin to be tested was weighed. Then different volumes of bile salt solution (1–50 ml) were added into the bottles. By changing the volumes of the bile salt solution added, a whole range of bile salt equilibrium concentrations was easily reached. They were shaken at room temperature (15°–25° C.) for more than 2 hours. Then they were filtered and the clear solutions were analyzed by High Performance Liquid Chromatography (HPLC) for which a perfect linear calibration curve was obtained under the used experimental conditions.

(b). Adsorption Studies in Simulated Intestine Contents and Extracted Pig Small Intestine The simulated small intestine solution with bile salt concentration about 100 mg/dl was prepared by dissolving each capsule of Cotazym-65B (Organon) in 60 ml distilled water. Pig small intestine was collected from freshly killed pigs. The contents of the small intestine were squeezed into a container and filtered to obtain a milky fluid for the adsorption studies. The pH of the above two was measured to be close to 7.0. About 3–5 mg of the resin was weighed into bottles of different sizes and each was pre-swollen with one-drop of distilled water. Different volumes of the solution were added into the resin bottles. They were shaken at 37° C. for 4 hours. 200 ul of each fluid was centrifuged. The upper clear solution was diluted 50 times and was analyzed by fluorescence.

EXAMPLE 1

A hydrophilic amine-containing resin was prepared as described above by grafting onto the cross-linked polymethylacrylate backbone ethylene diamine and was then converted to the hydrochloric form by washing with dilute aqueous HCl. This material, designated "unquaternized resin 1", was stirred or shaken with a $Na^+$-glycocholate solution in Tris buffer at initial concentration of 30–50 mg/dl for more than 2 hours. The amount of $Na^+$-glycocholate adsorbed was measured by HPLC as described above. The adsorption isotherm is shown in FIG. 1. At an equilibrium concentration of 0.4 mM, this resin adsorbed 4.5 mmol of $Na^+$-glycocholate per gram of resin.

EXAMPLE 2

Figure 2:
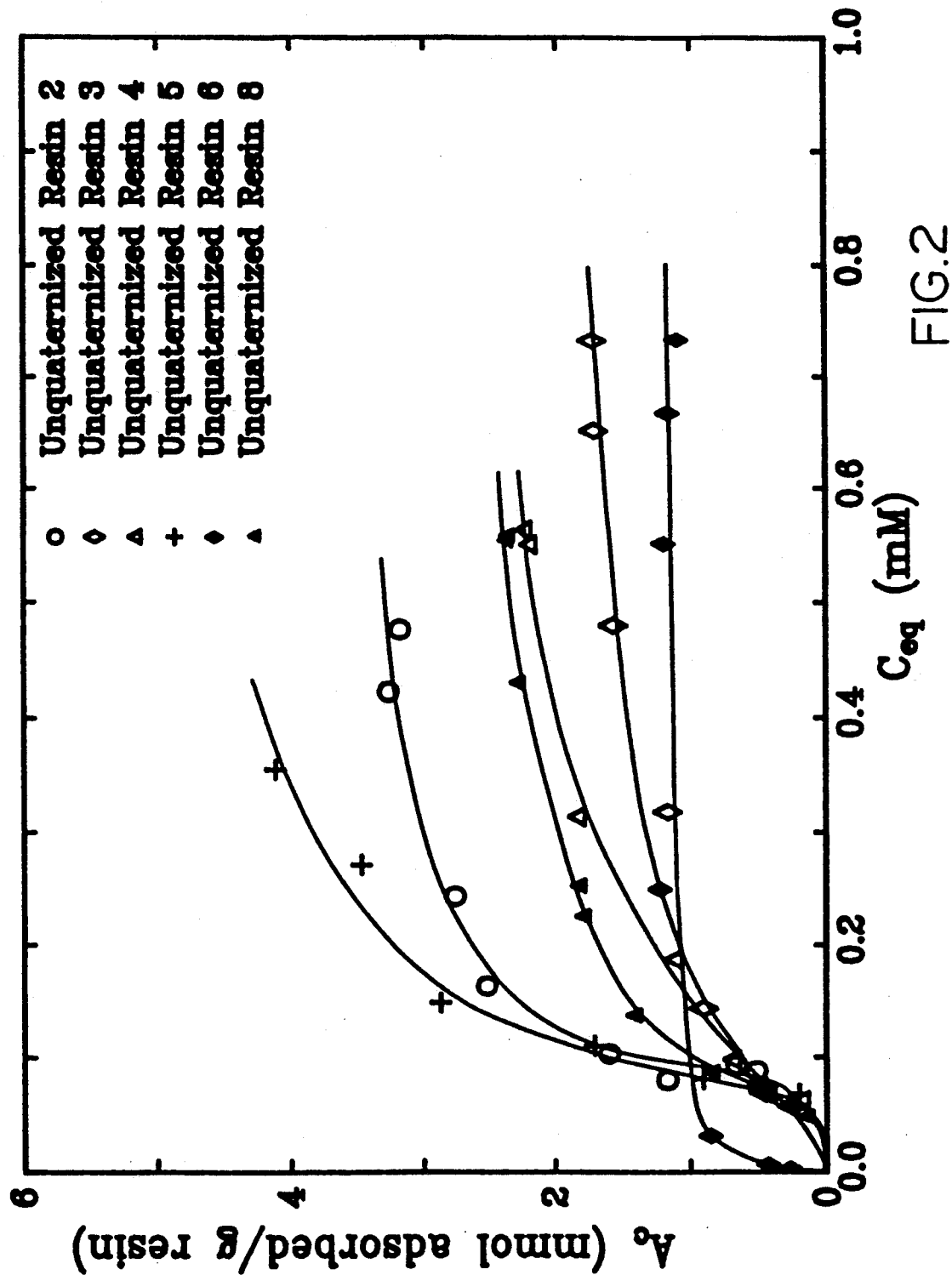

Example 1 was repeated except that diethylenetriamine instead of ethylene diamine was grafted onto the polymethylacrylate backbone. The product obtained, designated "unquaternized resin 2", adsorbed 3.2 mmol of $Na^+$-glycocholate per gram of resin at an equilibrium concentration of 0.4 mM. The adsorption isotherm is shown in FIG. 2.

EXAMPLE 3

Example 1 was repeated except that 1,4-diaminobutane instead of ethylene diamine was grafted onto the polymethylacrylate backbone. The product obtained, designated "unquaternized resin 3", adsorbed 1.5 mmol of $Na^+$-glycocholate per gram of resin at an equilibrium concentration of 0.4 mM. The adsorption isotherm is shown in FIG. 2.

EXAMPLE 4

Example 1 was repeated except that 1,6-hexanediamine instead of ethylene diamine was grafted onto the polymethylacrylate backbone. The product obtained, designated "unquaternized resin 4", adsorbed 2.0 mmol of $Na^+$-glycocholate per gram of resin at an equilibrium concentration of 0.4 mM. The adsorption isotherm is shown in FIG. 2.

EXAMPLE 5

Example 1 was repeated except that 1,3-diaminopropane instead of ethylene diamine was grafted onto the polymethylacrylate backbone. The product obtained, designated "unquaternized resin 5", adsorbed 4.2 mmol of $Na^+$-glycocholate per gram of resin at an equilibrium concentration of 0.4 mM. The adsorption isotherm is shown in FIG. 2.

EXAMPLE 6

Example 1 was repeated except than 1,12-diaminododecane instead of ethylene diamine was grafted onto the polymethylacrylate backbone. The product obtained, designated "unquaternized resin 6", adsorbed 1.2 mmol of $Na^+$-glycocholate per gram of resin at an equilibrium concentration of 0.4 mM. The adsorption isotherm is shown in FIG. 2.

EXAMPLE 7

Example 1 was repeated except that the amine-containing resin was quaternized with methyl iodide and then was converted to chloride form by washing with concentrated sodium chloride solution. The product obtained, designated "quaternized resin 1", adsorbed 1.7 mmol of $Na^+$-glycocholate per gram of resin at an equilibrium concentration of 0.4 mM. The adsorption isotherm is shown in FIG. 1.

EXAMPLE 8

Example 2 was repeated except that the amine-containing resin as quaternized and converted in the manner described in Example 7. The product obtained, designated "quaternized resin 2", adsorbed 3.0 mmol of $Na^+$-glycocholate per gram of resin at an equilibrium concentration of 0.4 mM. The adsorption isotherm is shown in FIG. 1.

EXAMPLE 9

Example 1 was repeated except that the triethylenetetramine instead of ethylene diamine was grafted onto the polymethylacrylate backbone and that the amine-containing resin was quaternized and converted the way mentioned in Example 7. The product obtained, designated "quaternized resin 7", adsorbed 3.2 mmol of $Na^+$-glycocholate per gram of resin at an equilibrium concentration of 0.4 mM. The adsorption isotherm is shown in FIG. 1.

EXAMPLE 10

Example 1 was repeated except that tris(2-aminoethyl) amine instead of ethylene diamine was grafted onto the polymethylacrylate backbone. The product obtained, designated "unquaternized resin 8", adsorbed 2.2 mmol of $Na^+$-glycocholate per gram of resin at an equilibrium concentration of 0.4 mM. The adsorption isotherm is shown in FIG. 2.

EXAMPLE 11

Figure 3:
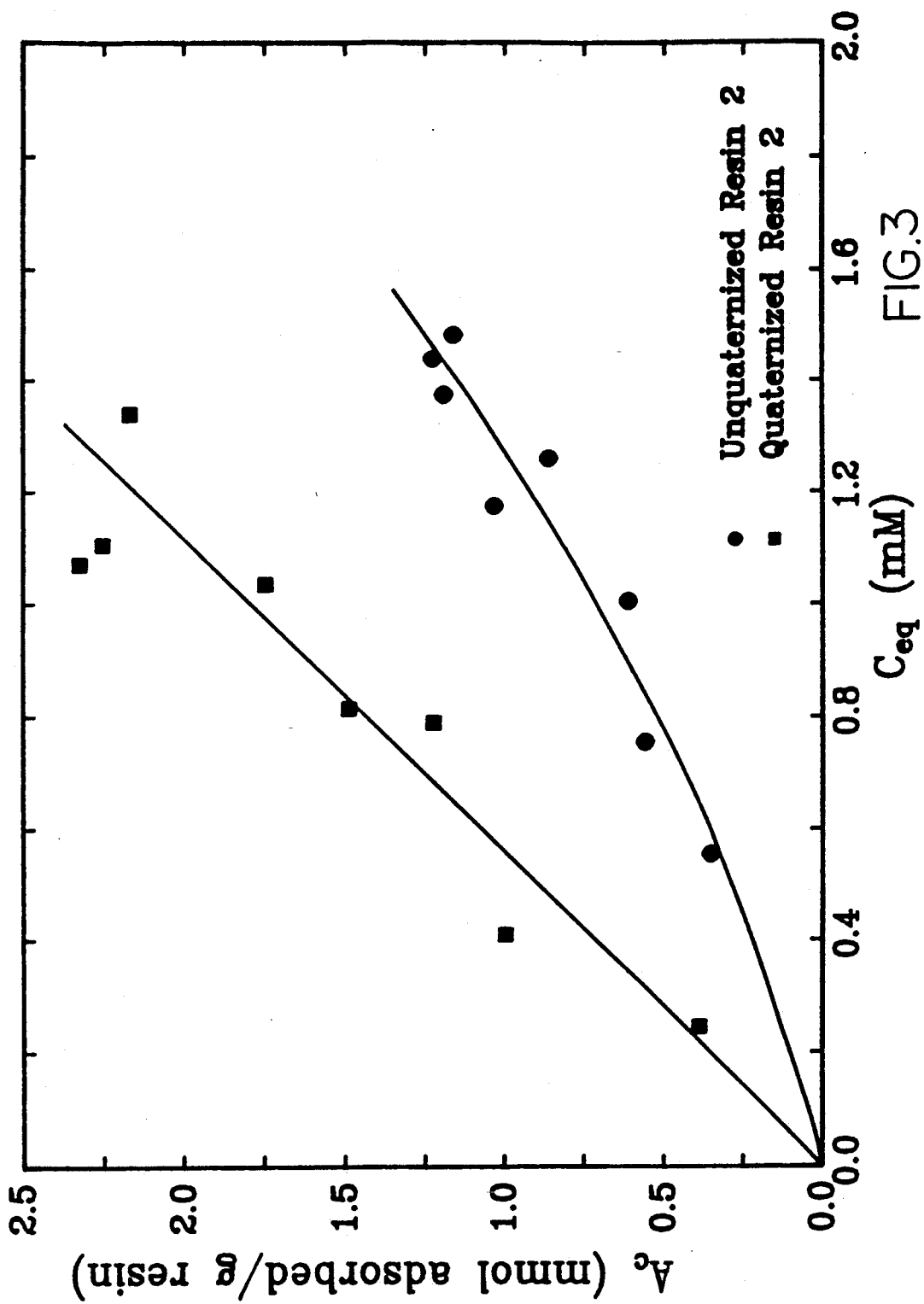
FIG. 3 shows bile salt adsorption isotherms in simulated small intestine contents.

The amine-containing resin of Example 2, designated "unquaternized resin 2", was stirred or shaken with a simulated small intestine solution as defined above for 4 hours at 37° C. and at $Na^+$-glycocholate initial concentration of about 100 mg/dl. The amount of $Na^{30}$ glycocholate adsorbed by this resin, as measured by fluorescence, was 0.7 mmol of $Na^+$-glycocholate per gram of resin at an equilibrium concentration of 1.0 mM. The adsorption isotherm is shown in FIG. 3.

EXAMPLE 12

The amine-containing resin of Example 8, designated "quaternized resin 2", was stirred or shaken with a simulated small intestine solution as defined above for 4 hours at 37° C. and at $Na^+$-glycocholate initial concentration of about 100 mg/dl. The amount of $Na^+$-glycocholate adsorbed by this resin, as measured by fluorescence, was 1.8 mmol of $Na^+$-glycocholate per gram of resin at an equilibrium concentration of 1.0 mM. The adsorption isotherm is shown in FIG. 3.

EXAMPLE 13

Figure 4:
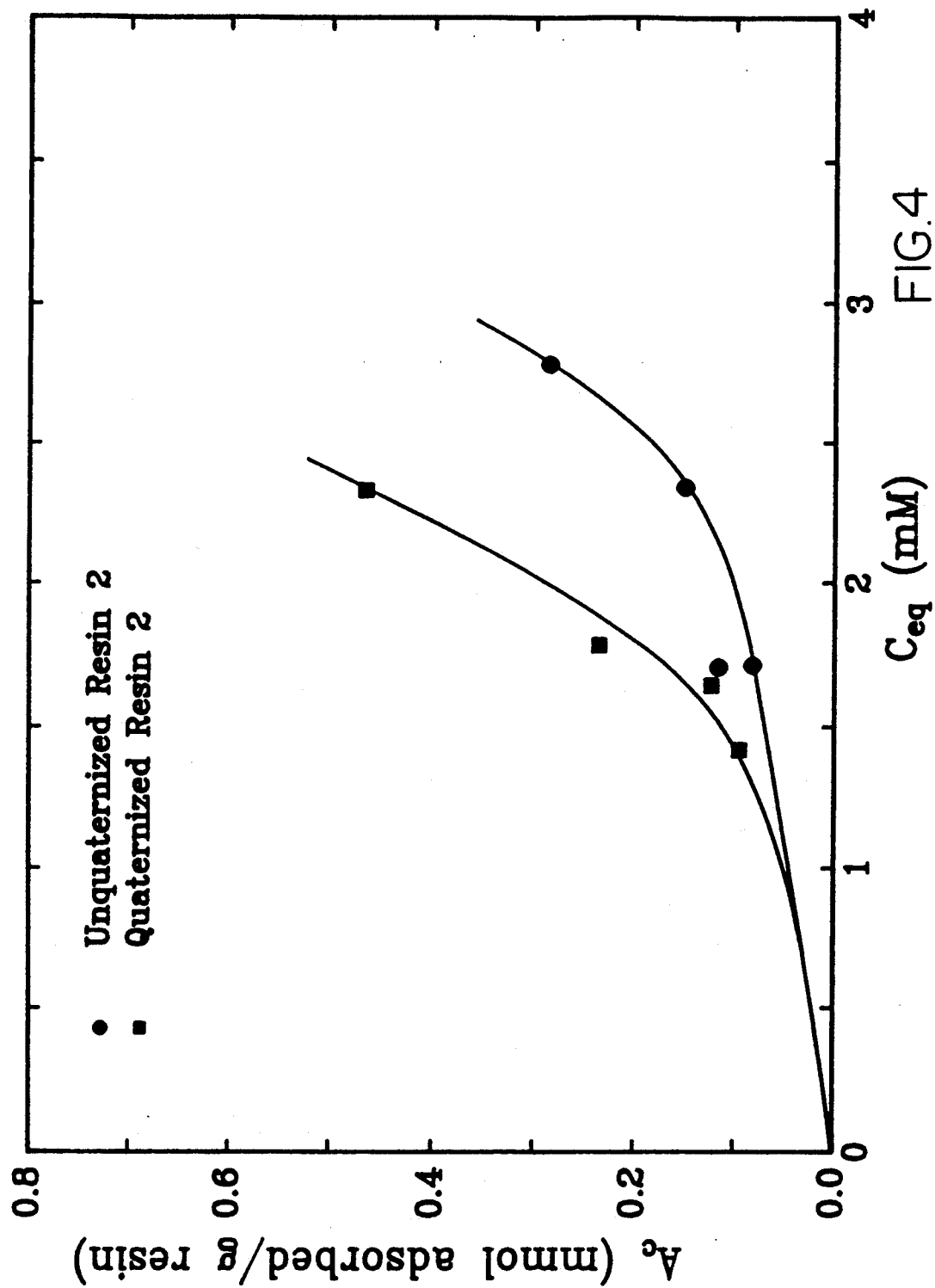
FIG. 4 shows bile salt adsorption isotherms in an extract from pig small intestine.

The amine-containing resins of Examples 2 and 8, designated "unquaternized resin 2" and "quaternized resin 2", respectively, were stirred or shaken with extracted pig small intestine as defined above for 4 hours at 37° C. and at a bile salt initial concentration of about 150 mg/dl. Good adsorption capacities were manifested in both cases at concentration above 2 mM/L. The adsorption isotherms are shown in FIG. 4.

The adsorption capacities of the amino-containing resins prepared in Examples 1 through 10 are summarized in the following Table:

TABLE 1

| Ex. No. | Product Designation | Structure | Adsorption Capacity (*) |
|---|---|---|---|
| 1 | Unquaternized Resin 1 | $P-(CH_2)_2N^+H_3Cl^-$ | 4.5 |
| 2 | Unquaternized Resin 2 | $P-[(CH_2)_2N^+H_2Cl^-]_2H$ | 3.2 |
| 3 | Unquaternized Resin 3 | $P-(CH_2)_4N^+H_3Cl^-$ | 1.5 |
| 4 | Unquaternized Resin 4 | $P-(CH_2)_6N^+H_3Cl^-$ | 2.0 |
| 5 | Unquaternized Resin 5 | $P-(CH_2)_3N^+H_3Cl^-$ | 4.2 |
| 6 | Unquaternized Resin 6 | $P-(CH_2)_{12}N^+H_3Cl^-$ | 1.2 |
| 7 | Quaternized Resin 1 | $P-(CH_2)_2N^+(CH_3)_3Cl^-$ | 1.7 |
| 8 | Quaternized Resin 2 | $P-[(CH_2)_2N^+(CH_3)_2Cl^-]_2CH_3$ | 3.0 |
| 9 | Quaternized Resin 7 | $P-[(CH_2)_2N^+(CH_3)_2Cl^-]_3CH_3$ | 3.2 |
| 10 | Unquaternized Resin 8 | $P-(CH_2)_2N^+HCl^-$ with branches $(CH_2)_2N^+H_3Cl^-$ and $(CH_2)_2N^+H_3Cl^-$ | 2.2 |

(*) mmol of sodium glycocholate adsorbed per gram of resin (at an equilibrium concentration of 0.4 mM).

As may be seen from FIGS. 1 and 2, the shapes of the isotherms are strongly dependent on the structure (hydrophobicity) of the sorbent. As the ionic strength of the buffer increases, the adsorption affinity decreases markedly. The adsorption by the unquaternized sorbents is strongly dependent on pH and is favoured by an increase in temperature and smaller particle size. It is also apparent that the preferred amine-containing resins of the invention have higher adsorption capacities, in vitro, than the commonly used cholestyramine and colestipol.

For any medical applications, especially by oral administration, the water-swellability of the material is often considered as a major evaluation parameter because most of the human fluids have high water contents. Generally, the more water-swellable the polymer material is, the more biocompatible it will be.

The measurements of the water-swellability were done in several 10 ml graduate cylinders. About 0.5 gram of the resin was weighed and put into the cylinder. After it was tapped for a while, the initial reading, volume of the resin, was taken and recorded. Then enough distilled water was added to the cylinder and let it stand for at least 24 hours. The final volume was taken. The resin was separated from the unabsorbed water. The swollen resin was weighed again. The swellability and the water content (adsorption capacity of water) were calculated, which were expressed as percentage of the volume change over the initial volume.

$$Swellability = (V_p - V_o)/V_o \times 100\%$$

$$Water\ content = (W_p - W_o)/W_o \times 100\%$$

where:

$V_o$ and $W_o$ are the original values
$V_p$ and $W_p$ are the values after swelling.

The results from these measurements are listed in the following Table:

TABLE 2

| Product | $H_2O$ swellability | $H_2O$ content |
|---|---|---|
| Unquaternized Resin 1 | 500% | 560% |
| Unquaternized Resin 2 | 220% | 240% |
| Unquaternized Resin 4 | 162% | 220% |

TABLE 2-continued

| Product | H₂O swellability | H₂O content |
|---|---|---|
| Quaternized Resin 1 | 260% | 460% |
| Quaternized Resin 2 | 338% | 320% |
| Quaternized Resin 4 | 150% | 260% |

It can be seen that the above materials are extremely water-swellable. For unquaternized resin 1, after swelling, its volume is five times larger than before, and can hold water five times more than its own weight. Other resins, both quaternized and unquaternized, have also shown tremendous H₂O swellabilities.

We claim:

1. A swellable, covalently cross-linked amine homopolymer comprising functional groups consisting of linear or branched amines having the chemical formula $$P-[(CH_2)_nNR]_mR \quad (Ia)$$

or

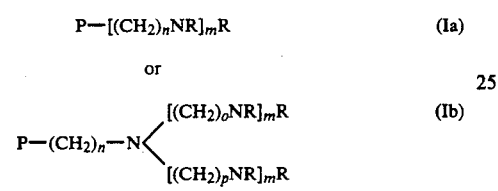

$$(Ib)$$

and pharmaceutically acceptable salts thereof having the chemical formula $$P-[(CH_2)_nN^+(R)_2]_mRmX^- \quad (Ic)$$

and

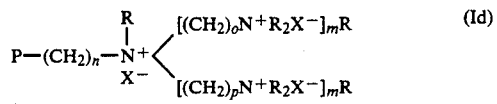

$$(Id)$$

wherein
P represents a hydrophilic, covalently cross-linked, non-digestible homopolymer backbone;
R is hydrogen or lower alkyl;
$X^-$ is a pharmaceutically acceptable anion;
m is an integer of 1 to 10 inclusive; and
n, o and p are, independent from one another, integers of 2 to 12, inclusive.

2. The covalently cross-linked, amine homopolymer of claim 1, having the chemical formula (Ia), and pharmaceutically acceptable salts thereof having the chemical formula (Ic), wherein
R is hydrogen or methyl;
m is 1, 2 or 3; and
n is 2 or 3.

3. The covalently cross-linked amine homopolymer of claim 1, having the chemical formula (Ia), and pharmaceutically acceptable salts thereof having the chemical formula (Ic), wherein
P represents a polyacrylamide resin.

4. The covalently cross-linked amine homopolymer of claim 1 having the chemical formula (Ib), and pharmaceutically acceptable salts thereof having the chemical formula (Id), wherein
R is hydrogen or methyl;
m is 1; and
n, o and p are each 2.

5. The covalently cross-linked amine homopolymer of claim 1 having the chemical formula (Ib), and pharmaceutically acceptable salts thereof having the chemical formula (Id), wherein
P represents a polyacrylamide resin.

6. A porous, non-digestible, covalently cross-linked amine homopolymer, comprising
the covalently cross-linked homopolymer of claim 1, wherein P comprises a porous, covalently cross-linked, non-digestible homopolymer.

7. The covalently cross-linked amine homopolymer of claim 1, having the chemical formula $$P-(CH_2)_2NH_2;$$

and protonated and quaternized derivatives thereof having the chemical formula $$P-(CH_2)_2N^+H_3X^-; \text{ and}$$

$$P-(CH_2)_2N^+(CH_3)_3X^-;$$

wherein
P represents a polyacrylamide resin; and
X comprises a pharmaceutically-acceptable anion.

8. The covalently cross-linked amine homopolymer of claim 1, having the chemical formula $$P-[(CH_2)_2NH]_2H;$$

and protonated and quaternized derivatives thereof having the chemical formula $$P-[(CH_2)_2N^+H_2]_2H.2X^-; \text{ and}$$

$$P-[(CH_2)_2N^+(CH_3)_2]_2CH_3.2X^-;$$

wherein
P represents a polyacrylamide resin; and
$X^-$ comprises a pharmaceutically-acceptable anion.

9. The covalently cross-linked amine homopolymer of claim 1, having the chemical formula $$P-[(CH_2)_2NH]_3H;$$

and protonated and quaternized derivatives thereof having the chemical formula $$P-[(CH_2)_2N^+H_2]_3H.3X^-; \text{ and}$$

$$P-[(CH_2)_2N^+(CH_3)_2]_3CH_3.3X^-;$$

wherein
P represents a polyacrylamide resin; and
$X^-$ comprises a pharmaceutically-acceptable anion.

10. The covalently cross-linked amine homopolymer of claim 1, having the chemical formula $$P-(CH_2)_3NH_2;$$

and a protonated derivative thereof having the chemical formula $$P-(CH_2)_3N^+H_3X^-;$$

wherein
P represents a polyacrylamide resin; and
$X^-$ comprises a pharmaceutically-acceptable anion.

11. The covalently cross-linked amine homopolymer of claim 1, having the chemical formula $P-(CH_2)_4NH_2;$ and a protonated derivative thereof having the chemical formula $P-(CH_2)_4N^+H_3X^-;$ wherein
P represents a polyacrylamide resin; and
$X^-$ comprises a pharmaceutically-acceptable anion.

12. The covalently cross-linked amine homopolymer of claim 1, having the chemical formula $P-(CH_2)_6NH_2;$ and a protonated derivative thereof having the chemical formula $P-(CH_2)_6N^+H_3X^-;$ wherein
P represents a polyacrylamide resin; and
$X^-$ comprises a pharmaceutically-acceptable anion.

13. The covalently cross-linked amine homopolymer of claim 1, having the chemical formula $P-(CH_2)_{12}NH_2;$ and a protonated derivative thereof having the chemical formula $P-(CH_2)_{12}N^+H_3X^-;$ wherein
P represents a polyacrylamide resin; and
$X^-$ comprises a pharmaceutically-acceptable anion.

* * * * *